United States Patent
Tsujimura et al.

(10) Patent No.: US 12,327,074 B2
(45) Date of Patent: Jun. 10, 2025

(54) SIMULATION APPARATUS AND CREATION METHOD OF THERMAL EQUIVALENT CIRCUIT

(71) Applicants: KABUSHIKI KAISHA TOSHIBA, Tokyo (JP); TOSHIBA ELECTRONIC DEVICES & STORAGE CORPORATION, Tokyo (JP)

(72) Inventors: Toshihiro Tsujimura, Ota Tokyo (JP); Daisuke Ando, Yokohama Kanagawa (JP); Hitoshi Imi, Yokohama Kanagawa (JP); Takahiro Aoki, Gyoda Saitama (JP)

(73) Assignees: Kabushiki Kaisha Toshiba, Tokyo (JP); Toshiba Electronic Devices & Storage Corporation, Tokyo (JP)

( * ) Notice: Subject to any disclaimer, the term of this patent is extended or adjusted under 35 U.S.C. 154(b) by 639 days.

(21) Appl. No.: 17/692,136

(22) Filed: Mar. 10, 2022

(65) Prior Publication Data
US 2023/0088851 A1    Mar. 23, 2023

(30) Foreign Application Priority Data
Sep. 17, 2021 (JP) .................. 2021-152306

(51) Int. Cl.
*G06F 30/3308* (2020.01)
*G01N 25/18* (2006.01)
(Continued)

(52) U.S. Cl.
CPC ......... *G06F 30/3308* (2020.01); *G01N 25/18* (2013.01); *G06F 30/337* (2020.01);
(Continued)

(58) Field of Classification Search
CPC .. G06F 30/3308; G06F 30/337; G06F 30/367; G06F 30/373; G06F 30/398; G06F 2119/08; G01N 25/18
(Continued)

(56) References Cited

U.S. PATENT DOCUMENTS

| | | | |
|---|---|---|---|
| 5,262,673 A | | 11/1993 | Mikoshiba et al. |
| 6,138,893 A | * | 10/2000 | Caletka ............... B23K 3/08 228/103 |

(Continued)

FOREIGN PATENT DOCUMENTS

| | | | | |
|---|---|---|---|---|
| CN | 106104234 B | * | 10/2019 | ............ G01K 7/01 |
| CN | 112287510 A | * | 1/2021 | ............ G01K 13/00 |

(Continued)

OTHER PUBLICATIONS

ROHM Co., Ltd., "About Thermal Dynamic Model", Apr. 28, 2020, 3 pages https://techweb.rohm.co.jp/knowledge/simulation/s-simulation/01-s-simulation/9029 (with Translation).
(Continued)

*Primary Examiner* — Phallaka Kik
(74) *Attorney, Agent, or Firm* — Kim & Stewart LLP (57) ABSTRACT

According to one embodiment, a simulation apparatus is disclosed. The simulation apparatus includes a storage device storing data relating to a thermal equivalent circuit of a semiconductor device. The simulation apparatus further includes an estimation device estimating a time-dependent change in thermal characteristics of the semiconductor device by using the data. The thermal equivalent circuit includes a first thermal equivalent circuit corresponding to a lower-surface-side part of the semiconductor device. The thermal equivalent circuit further includes a second thermal
(Continued)

equivalent circuit connected to the first thermal equivalent circuit and corresponding to an upper-surface-side part of the semiconductor device.

2 Claims, 6 Drawing Sheets

(51) Int. Cl.
    *G06F 30/337*     (2020.01)
    *G06F 30/367*     (2020.01)
    *G06F 30/373*     (2020.01)
    *G06F 30/398*     (2020.01)
    *G06F 119/08*     (2020.01)

(52) U.S. Cl.
    CPC .......... *G06F 30/367* (2020.01); *G06F 30/373* (2020.01); *G06F 30/398* (2020.01); *G06F 2119/08* (2020.01)

(58) Field of Classification Search
    USPC ............................ 716/106, 111, 136; 703/14
    See application file for complete search history.

(56) References Cited

U.S. PATENT DOCUMENTS

| | | | |
|---|---|---|---|
| 6,238,086 B1 | 5/2001 | Mikubo et al. | |
| 8,633,726 B2 | 1/2014 | Koh et al. | |
| 9,910,947 B1* | 3/2018 | Kao | ...................... G06F 30/367 |
| 10,192,009 B2 | 1/2019 | Goverde et al. | |
| 10,896,279 B2* | 1/2021 | Proulx | ................... G06F 30/20 |
| 2001/0045445 A1* | 11/2001 | Caletka | ................ H05K 1/0201 |
| | | | 228/103 |
| 2011/0015897 A1* | 1/2011 | Li | ...................... G01R 31/2851 |
| | | | 702/182 |
| 2018/0314782 A1* | 11/2018 | Proulx | .................. G06F 30/367 |
| 2021/0026929 A1* | 1/2021 | Zheng | ..................... H02P 29/68 |
| 2021/0271473 A1 | 9/2021 | Imi et al. | |
| 2022/0034958 A1* | 2/2022 | Denk | ................. G01R 31/2834 |

FOREIGN PATENT DOCUMENTS

| | | |
|---|---|---|
| JP | H03-257953 A | 11/1991 |
| JP | 2002-251421 A | 9/2002 |
| JP | 3501644 B2 | 3/2004 |
| JP | 2005-190262 A | 7/2005 |
| JP | 2006-294748 A | 10/2006 |
| JP | 2009-142146 A | 6/2009 |
| JP | 2012-73752 A | 4/2012 |
| JP | 5528366 B2 | 6/2014 |
| JP | 2016-077137 A | 5/2016 |
| JP | 6573809 B2 | 9/2019 |
| JP | 2021-140755 A | 9/2021 |
| JP | 2022-33586 A | 3/2022 |
| WO | WO-2015132217 A1 * | 9/2015 ............... G01K 7/01 |

OTHER PUBLICATIONS

Ono, Satoshi et al., "Steady and Transient Thermal Simulation of GaN Devices for High-Speed Switching Applications", Journal of The Japan Institute of Electronics Packaging, vol. 17, No. 6, 2014, pp. 484-491 with English machine translation, 24 pages. DOI: 10.5104/jiep.17.484, https://www.jstage.jst.go.jp/article/jiep/17/6/17_484/_pdf.

Notice of Reasons for Refusal (Office Action) mailed Jul. 23, 2024 in Japanese Patent Application No. 2021-152306 with English machine translation, 10 pages.

* cited by examiner

SIMULATION APPARATUS AND CREATION METHOD OF THERMAL EQUIVALENT CIRCUIT

CROSS-REFERENCE TO RELATED APPLICATIONS

This application is based upon and claims the benefit of priority from Japanese Patent Application No. 2021-152306, filed Sep. 17, 2021, the entire contents of which are incorporated herein by reference.

FIELD

Embodiments described herein relate generally to a simulation apparatus and a creation method of a thermal equivalent circuit.

BACKGROUND

In development of semiconductor devices, verification of a time-dependent change in thermal characteristics of a designed semiconductor device is carried out. This verification is carried out by using, for example, a simulation apparatus.

DETAILED DESCRIPTION

In general according to one embodiment, a simulation apparatus is disclosed. The simulation apparatus includes a storage device that stores data relating to a thermal equivalent circuit of a semiconductor device. The simulation apparatus further includes an estimation device that estimates a time-dependent change in thermal characteristics of the semiconductor device by using the data. The thermal equivalent circuit includes a first thermal equivalent circuit corresponding to a lower-surface-side part of the semiconductor device. The thermal equivalent circuit further includes a second thermal equivalent circuit connected to the first thermal equivalent circuit and corresponding to an upper-surface-side part of the semiconductor device.

Embodiments will be described hereinafter with reference to the accompanying drawings. The drawings are schematic or conceptual drawings, and dimensions and ratios are not necessarily the same as those in reality. Further, in the drawings, the same reference symbols (including those having different subscripts) denote the same or corresponding parts, and overlapping explanations thereof will be made as necessary. In addition, as used in the description and the appended claims, what is expressed by a singular form shall include the meaning of "more than one".

Figure 1:
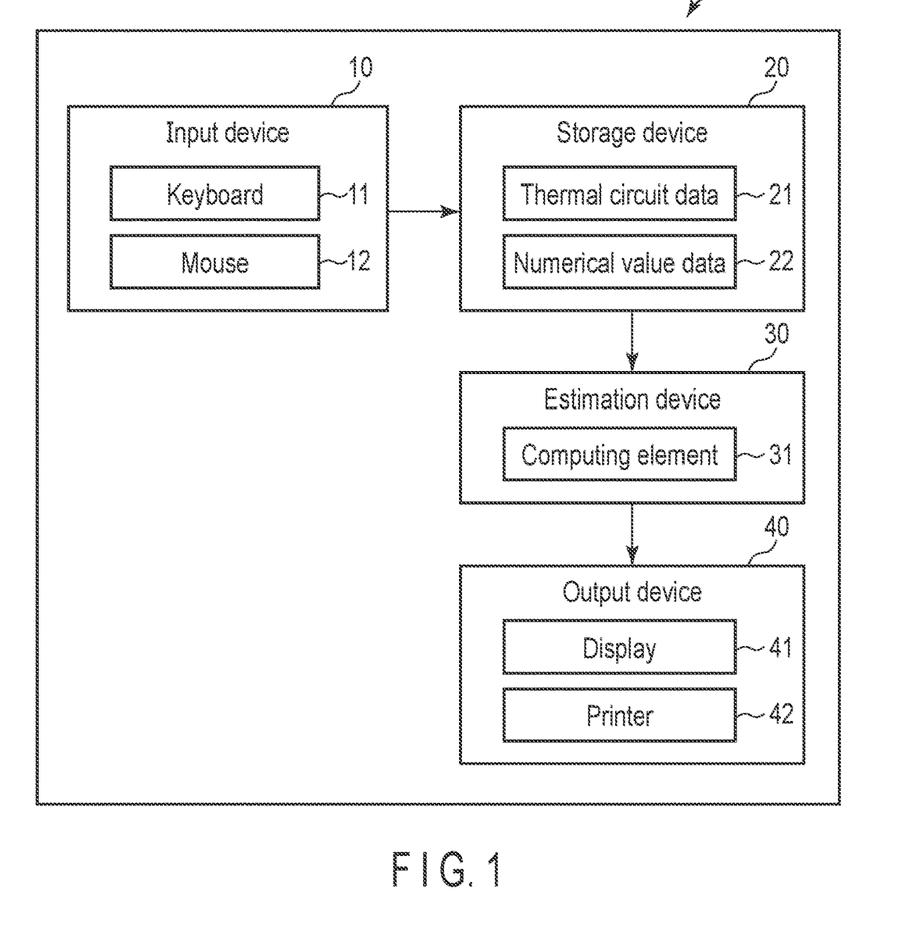
FIG. 1 is a block diagram showing an example of a hardware configuration of a simulation apparatus according to an embodiment.

FIG. 1 is a block diagram showing an example of a hardware configuration of a simulation apparatus 1 according to an embodiment.

The simulation apparatus 1 estimates a time-dependent change in thermal characteristics (transient thermal response) of a designed semiconductor device by calculation. The simulation apparatus 1 may estimate electrical characteristics of the designed semiconductor device, in addition to the time-dependent change in the thermal characteristics of the designed semiconductor device by calculation.

As shown in FIG. 1, the simulation apparatus 1 includes an input device 10, a storage device 20, an estimation device 30, and an output device 40.

The input device 10 is used for inputting a type of the semiconductor device, a thermal parameter value of the semiconductor device, and the like. The input device 10 includes, for example, a keyboard 11 and a mouse 12. The type of the semiconductor device is, for example, an integrated circuit device in which basic elements are MOSFETs, or an integrated circuit device in which basic elements are diodes. Thermal parameters includes, for example, the temperature of an atmosphere in which the semiconductor device is used (ambient temperature), or power consumption of the semiconductor device.

The storage device 20 stores data, programs, and the like in a readable manner. In the present embodiment, data relating to a thermal equivalent circuit of the semiconductor device (hereinafter "thermal circuit data") 21 and data relating to thermal parameter values which is input from the input device 10 (hereinafter "numerical data") 22 are stored in the storage device 20 in a readable manner.

In a case where the time-dependent change in the thermal characteristics of the semiconductor device and the electrical characteristics of the semiconductor device are to be estimated, data relating to an electrical equivalent circuit of the semiconductor device as well as the thermal circuit data is stored in the storage device 20 in a readable manner.

The storage device 20 includes, for example, a magnetic storage device or a semiconductor storage device. The magnetic storage device is, for example, a hard disk device. The semiconductor storage device is, for example, a nonvolatile semiconductor device. The nonvolatile semiconductor device is, for example, a solid state drive (SSD) comprising a NAND flash memory. A phase change random access memory (PRAM), a resistive random access memory (ReRAM), or a ferroelectric random access memory (FeRAM) may be used instead of the SSD.

The estimation device 30 estimates the time-dependent change in the thermal characteristics of the semiconductor device by simulation (calculation). The estimation device 30 includes a computing element 31 that carries out the calculation set forth above. The computing element 31 includes, for example, a central processing unit (CPU). The computing element 31 estimates the time-dependent change in the thermal characteristics of the designed semiconductor device by calculation by using the thermal circuit data 21 and the numerical data 22 which are read out from the storage device 20, and a program necessary for the simulation.

The program necessary for the simulation (simulation program) is stored in the simulation apparatus 1 in a readable manner. For example, the simulation program is stored in the storage device 20 in a readable manner.

In a case where the estimation device 30 includes a storage device (not illustrated), the simulation program may be stored in the storage device set forth above in a readable manner.

Alternatively, the program may be stored in an external storage device (not illustrated) in a readable manner when the external storage device can be connected to the simulation apparatus 1.

The simulation program is, for example, a SPICE (Simulation Program with Integrated Circuit Emphasis) program. The simulation program is provided, for example, through the Internet.

The output device 40 outputs the time-dependent change in the thermal characteristics (simulation result) of the semiconductor device estimated by the estimation device 30 in a visible form. The output device 40 includes, for example, a display 41 or a printer 42.

It is noted that the output device 40 may be not included in the simulation apparatus 1. In such a case, an output device connectable to the simulation apparatus 1 is prepared when the simulation result is to be output.

Figure 2:
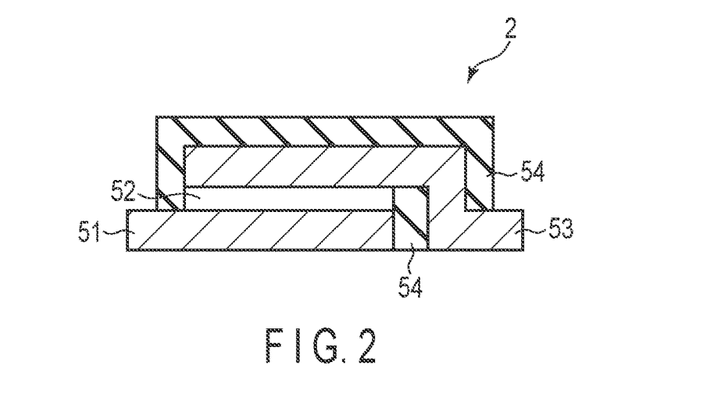
FIG. 2 is a cross-sectional view showing an example of a semiconductor device.

An example of a semiconductor device subjected to a simulation by the simulation apparatus 1 will then be described. FIG. 2 is a cross-sectional view of an example of a semiconductor device 2.

The semiconductor device 2 includes a first frame 51, a semiconductor chip 52, a second frame 53, and a molding resin 54. The semiconductor chip 52 is sealed by the first frame 51, the second frame 53, and the molding resin 54. The semiconductor chip 52 includes, for example, an in-vehicle semiconductor device or a power semiconductor device. An example of the in-vehicle semiconductor device is an in-vehicle MOSFET. An example of the power semiconductor device is a power diode. A material of the first frame 51 and second frame 53 is, for example, copper.

Figure 3:
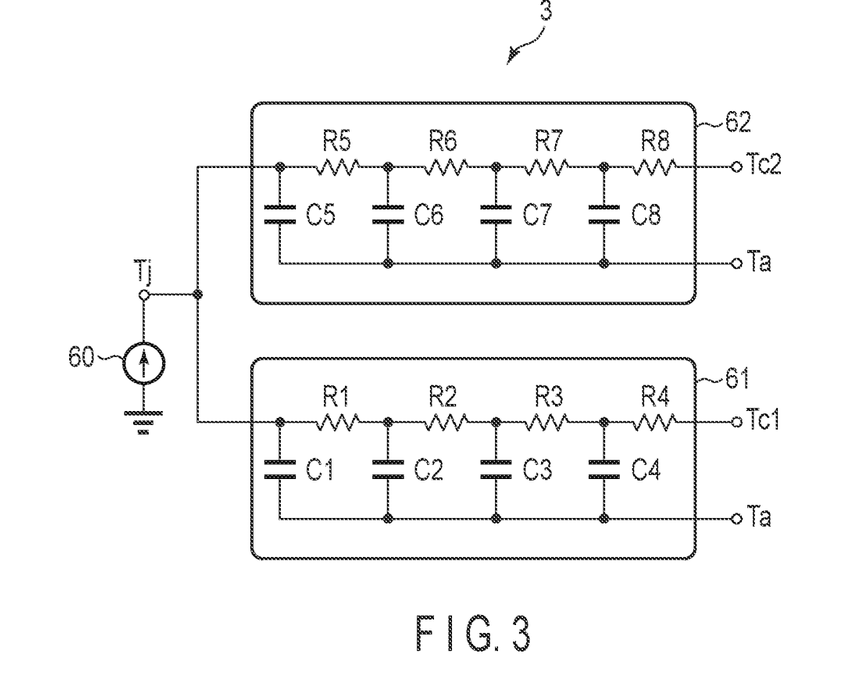
FIG. 3 is a circuit diagram showing an example of a thermal equivalent circuit according to an embodiment.

FIG. 3 is a circuit diagram of an example of a thermal equivalent circuit 3 according to an embodiment of the semiconductor device 2.

The thermal equivalent circuit 3 includes a first thermal equivalent circuit 61 of a Cauer type, and a second thermal equivalent circuit 62 of a Cauer type connected to the first thermal equivalent circuit 61.

The first thermal equivalent circuit 61 represents a thermal equivalent circuit corresponding to a lower-surface-side part of the semiconductor device 2. In the example of FIG. 2, the lower-surface-side part of the semiconductor device 2 includes a lower surface of the semiconductor chip 52, the first frame 51 under the lower surface of the semiconductor chip 52, and the molding resin 54 in contact with the first frame 51.

The first thermal equivalent circuit 61 includes a first resistor R1, a second resistor R2, a third resistor R3, a fourth resistor R4, a first capacitor C1, a second capacitor C2, a third capacitor C3, and a fourth capacitor C4.

A terminal on the left of the first resistor R1 is connected to a terminal Tj. A current corresponding to power consumption of the semiconductor device 2 is input to the terminal Tj. Reference numeral 60 in FIG. 3 denotes a current source of the current corresponding to the power consumption. A terminal on the right of the fourth resistor R4 is connected to a terminal Tc1. A voltage corresponding to the surface temperature of a lower surface of the first frame 51 (case temperature) is applied to the terminal Tc1.

As shown in FIG. 3, the second resistor R2 and the third resistor R3 between the first resistor R1 and the fourth resistor R4 are connected in series.

The first resistor R1 corresponds to the thermal resistance of the lower surface of the semiconductor chip 52. The second resistor R2 corresponds to the thermal resistance of the first frame 51 under the lower surface of the semiconductor chip 52. The third resistor R3 corresponds to the thermal resistance of the molding resin 54 in contact with the first frame 51. The fourth resistor R4 corresponds to an adjustment thermal resistance for increasing impedance between the terminal Tc1 and a terminal Ta when no heat comes in or goes out of the lower surface of the semiconductor device 2.

An upper terminal of the first capacitor C1 is connected to the terminal on the left of the first resistor R1. An upper terminal of the second capacitor C2 is connected to a connection node between the first resistor R1 and the second resistor R2. An upper terminal of the third capacitor C3 is connected to a connection node between the second resistor R2 and the third resistor R3. An upper terminal of the fourth capacitor C4 is connected to a connection node between the third resistor R3 and the fourth resistor R4.

In addition, a terminal of lower-side of the first capacitor C1, a terminal of lower-side of the second capacitor C2, a terminal of lower-side of the third capacitor C3, and a terminal of lower-side of the fourth capacitor C4 are all connected to the terminal Ta. A voltage corresponding to the temperature of an atmosphere around the semiconductor device 2 (ambient temperature) is applied to the terminal Ta.

The first capacitor C1 corresponds to the heat capacity of the lower surface of the semiconductor chip 52. The second capacitor C2 corresponds to the heat capacity of the first frame 51 under the lower surface of the semiconductor chip 52. The third capacitor C3 corresponds to the heat capacity of the molding resin 54 in contact with the first frame 51. The fourth capacitor C4 is an adjustment heat capacity for increasing the impedance between the terminal Tc1 and the terminal Ta when no heat comes in or goes out of the lower surface of the semiconductor device 2.

The second thermal equivalent circuit 62 is a thermal equivalent circuit representing an upper-surface-side part of the semiconductor device 2. In the example of FIG. 2, the upper-surface-side part of the semiconductor device 2 includes an upper surface of the semiconductor chip 52, the second frame 53 on the upper surface of the semiconductor chip 52, and the molding resin 54 on a top of the second frame 53.

The second thermal equivalent circuit 62 includes a fifth resistor R5, a sixth resistor R6, a seventh resistor R7, an eighth resistor R8, a fifth capacitor C5, a sixth capacitor C6, a seventh capacitor C7, and an eighth capacitor C8.

A terminal on the left of the fifth resistor R5 is connected to the terminal Tj. A terminal on the right of the eighth resistor R8 is connected to a terminal Tc2. A voltage corresponding to the surface temperature of an upper surface of the molding resin 54 (case temperature) is applied to the terminal Tc2.

As shown in FIG. 3, the sixth resistor R6 and the seventh resistor R7 between the fifth resistor R5 and the eighth resistor R8 are connected in series.

An upper terminal of the fifth capacitor C5 is connected to the terminal on the left of the fifth resistor R5. An upper terminal of the sixth capacitor C6 is connected to a connection node between the fifth resistor R5 and the sixth resistor R6. An upper terminal of the seventh capacitor C7 is connected to a connection node between the sixth resistor R6 and the seventh resistor R7. An upper terminal of the eighth capacitor C8 is connected to a connection node between the seventh resistor R7 and the eighth resistor R8.

A lower terminal of the fifth capacitor C5, a lower terminal of the sixth capacitor C6, a lower terminal of the seventh capacitor C7, and a lower terminal of the eighth capacitor C8 are all connected to the terminal Ta.

The fifth resistor R5 corresponds to the thermal resistance of the upper surface of the semiconductor chip 52. The sixth resistor R6 corresponds to the thermal resistance of the second frame 53 on the upper surface of the lower surface of the semiconductor chip 52. The seventh resistor R7 corresponds to the thermal resistance of the molding resin 54 on the top of the second frame 53. The eighth resistor R8 is an adjustment thermal resistance for increasing impedance between the terminal Tc2 and the terminal Ta when no heat comes in or goes out of the upper surface of the semiconductor device 2.

The fifth capacitor C5 corresponds to the heat capacity of the upper surface of the semiconductor chip 52. The sixth capacitor C6 corresponds to the heat capacity of the second frame 53 on the upper surface of the semiconductor chip 52. The seventh capacitor C7 corresponds to the heat capacity of the molding resin 54 on the top of the second frame 53. The eighth capacitor C8 is an adjustment heat capacity for increasing the impedance between the terminal Tc2 and the terminal Ta when no heat comes in or goes out of the upper surface of the semiconductor device 2.

The number of resistors and capacitors which constitute the first thermal equivalent circuit 61, and the number of resistors and capacitors which constitute the second thermal equivalent circuit 62 depend on the structure of the semiconductor device subjected to the simulation. In general, the more complex the structure becomes, the greater the number of resistors and capacitors is.

Figure 4:
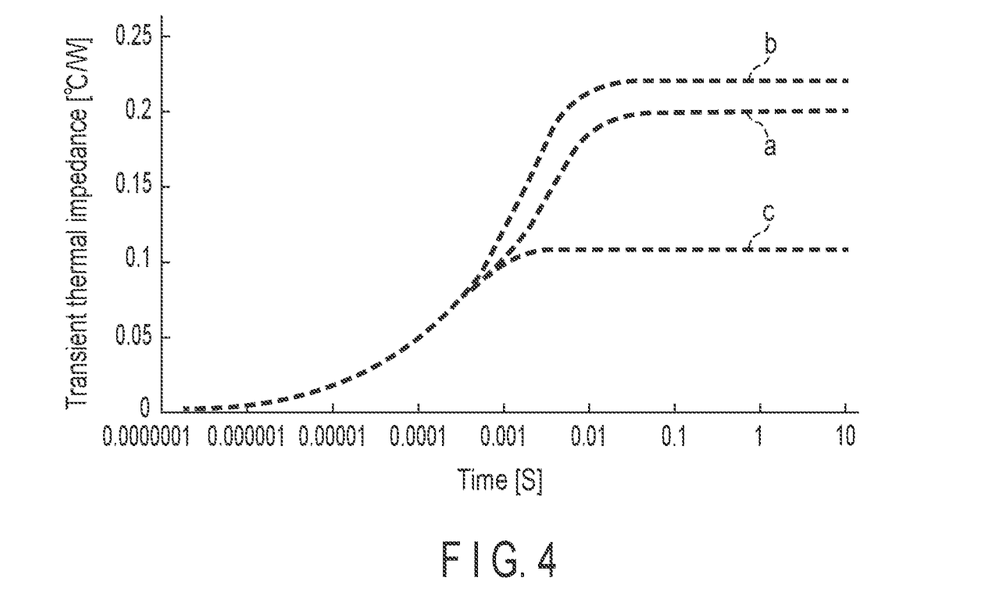
FIG. 4 is a diagram showing time-dependent changes in thermal characteristics of a semiconductor device which are estimated by using a simulation apparatus according to an embodiment.

FIG. 4 is a diagram showing time-dependent changes in thermal characteristics of the semiconductor device 2 which are estimated by using the simulation apparatus 1.

A curve a represents a time-dependent change in the thermal characteristics when the heat is dissipated from the lower surface of the semiconductor device 2 in a case where the heat dissipates from one of the lower surface and upper surface of the semiconductor device 2. The lower surface of the semiconductor device 2 is the lower surface of the first frame 51. The upper surface of the semiconductor device 2 is the upper surface of the molding resin 54. Hereinafter, the heat dissipation from the lower surface of the semiconductor device 2 is referred to as a lower surface heat dissipation.

A curve b represents a time-dependent change in the thermal characteristics when the heat is dissipated from the upper surface of the semiconductor device 2 in a case where the heat dissipates from one of the lower surface and upper surface of the semiconductor device 2. Hereinafter, the heat dissipation from the upper surface of the semiconductor device 2 is referred to as an upper surface heat dissipation.

A curve c represents a time-dependent change in the thermal characteristics when the heat is dissipated from both of the lower surface and the upper surface of the semiconductor device 2. Hereinafter, the heat dissipation from both of the lower surface and the upper surface of the semiconductor device 2 is referred to as a double-surface heat dissipation.

Figure 5:
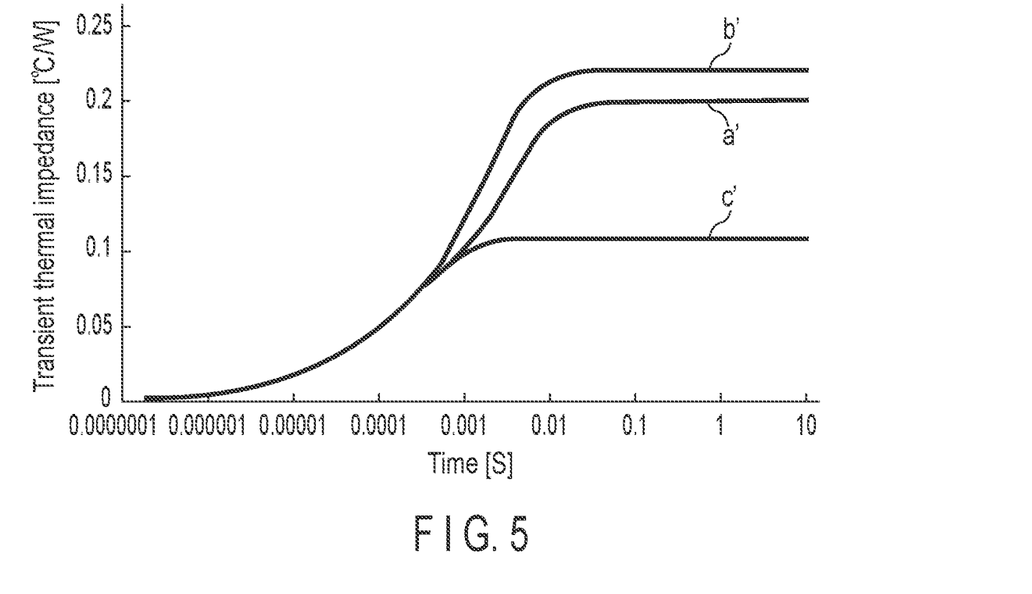
FIG. 5 is a diagram showing time-dependent changes in thermal characteristics of a semiconductor device which are calculated by a thermal fluid analysis employing a finite element method.

FIG. 5 is a diagram showing time-dependent changes in thermal characteristics (analysis results) of the semiconductor device 2 which are calculated by a thermal fluid analysis. The thermal fluid analysis can be carried out by using, for example, a finite element method, a finite volume method, or a finite difference method. The time-dependent changes in the thermal characteristics shown in FIG. 5 is referred to as a transient thermal impedance or transient thermal response. It is noted that the same time-dependent changes in the thermal characteristics shown in FIG. 5 can be obtained also by actual measurement.

A curve a' represents a time-dependent change in the thermal characteristics of the semiconductor device 2 with the lower surface heat dissipation. A curve b' represents a time-dependent change in the thermal characteristics of the semiconductor device 2 with the upper surface heat dissipation. A curve c' represents a time-dependent change in the thermal characteristics of the semiconductor device 2 with the double-surface heat dissipation.

FIG. 4 and FIG. 5 demonstrate the following facts. In the case of lower surface heat dissipation, the curve a representing a simulation result substantially matches the curve a' representing an analysis result. In the case of upper surface heat dissipation, the curve b representing a simulation result substantially matches the curve b' representing an analysis result. In the case of double-surface heat dissipation, the curve c representing a simulation result substantially matches the curve c' representing an analysis result. It is concluded from this observation that in each of the cases of the lower surface heat dissipation, the upper surface heat dissipation, and the double-surface heat dissipation, the simulation apparatus 1 has estimation accuracy necessary for estimating the time-dependent changes in the thermal characteristics of the designed semiconductor device.

In this manner, the simulation apparatus 1 can accurately estimate the time-dependent changes in the thermal characteristics in heat dissipation in the one-dimensional direction and the two-dimensional direction. It can be said, therefore, that the simulation apparatus 1 is useful for verifying the time-dependent changes in the thermal characteristics of the semiconductor device.

Using the simulation apparatus 1 allows verification of time-dependent changes in the thermal characteristics for any given combination of the time-dependent change in the thermal characteristics of the lower surface heat dissipation, the time-dependent change in the thermal characteristics of the upper surface heat dissipation, and the time-dependent change in the thermal characteristics of the double-surface heat dissipation.

According to the present embodiment, it is unnecessary to prepare a dedicated simulation apparatus for estimating the time-dependent change in the thermal characteristics of the lower surface heat dissipation, a dedicated simulation apparatus for estimating the time-dependent change in the thermal characteristics of the upper surface heat dissipation, and a dedicated simulation apparatus for estimating the time-dependent change in the thermal characteristics of the double-surface heat dissipation. The cost needed for preparing the simulation apparatus, therefore, can be reduced.

Figure 6:
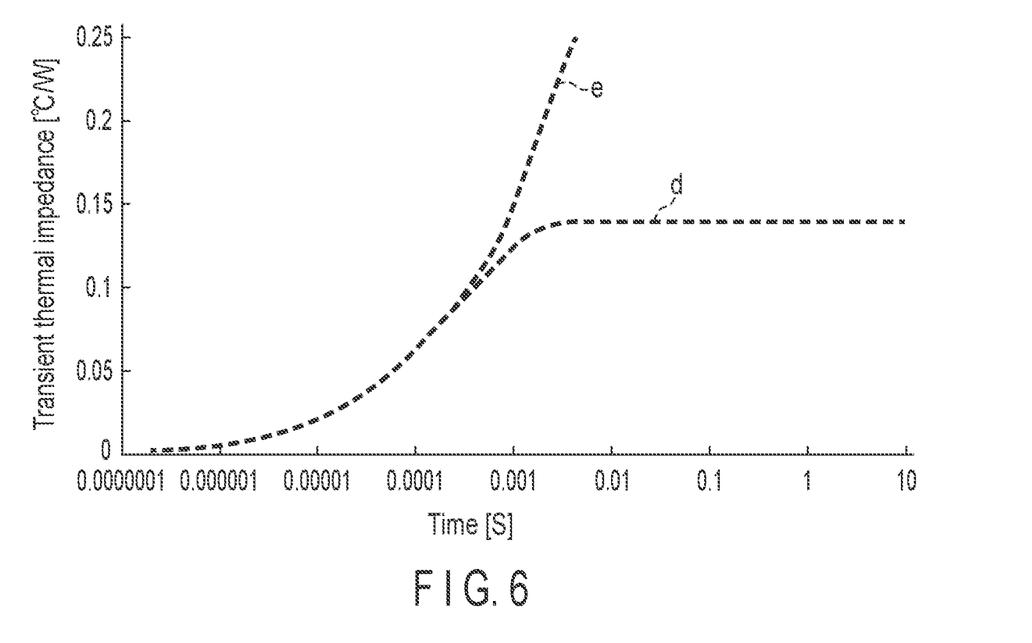
FIG. 6 is a diagram showing another time-dependent changes in thermal characteristics of a semiconductor device which are estimated by using a simulation apparatus according to an embodiment.

FIG. 6 is a diagram showing another time-dependent changes in thermal characteristics (simulation results) of the semiconductor device 2 which are estimated by using the simulation apparatus 1.

In FIG. 6, a curve d represents a time-dependent change in the thermal characteristics of the semiconductor device 2 in a state where heat comes in and goes out of its lower surface and upper surface (heat dissipation state). A curve e represents a time-dependent change in the thermal characteristics of the semiconductor device 2 in a state where no heat comes in or goes out of its lower surface and upper surface (adiabatic state).

Figure 7:
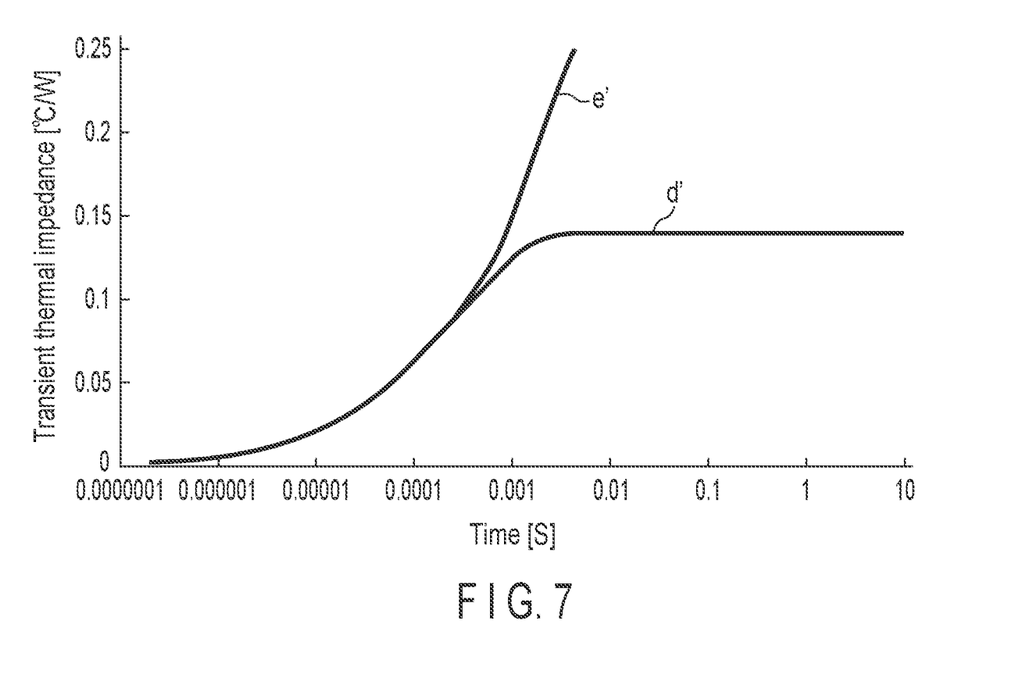
FIG. 7 is a diagram showing another time-dependent changes in thermal characteristics of a semiconductor device which are calculated by a thermal fluid analysis employing a finite element method.

FIG. 7 is a diagram showing another time-dependent changes in thermal characteristics (analysis results) of the semiconductor device 2 which are calculated by using a thermal fluid analysis employing a finite element method (FEM).

In FIG. 7, a curve d' represents a time-dependent change in the thermal characteristics of the semiconductor device 2 in the heat dissipation state, and a curve e' represents a time-dependent change in the thermal characteristics of the semiconductor device 2 in the adiabatic state.

FIG. 6 and FIG. 7 demonstrate the following facts. In the case of the heat dissipation state, the curve d representing a simulation result substantially matches the curve d' representing an analysis result. In the case of the adiabatic state, the curve e representing a simulation result substantially matches the curve e' representing an analysis result. It is concluded from this observation that in each of the cases of the heat dissipation state and the adiabatic state, the simulation apparatus 1 has estimation accuracy necessary for estimating a time-dependent change in the thermal characteristics of the designed semiconductor device.

In this manner, the simulation apparatus 1 can accurately estimate the time-dependent changes in the thermal characteristics in both cases of the heat dissipation state and the adiabatic state. Thus, it can be said that the simulation apparatus 1 is useful for verifying the time-dependent change in the thermal characteristics of the semiconductor device.

Figure 8:
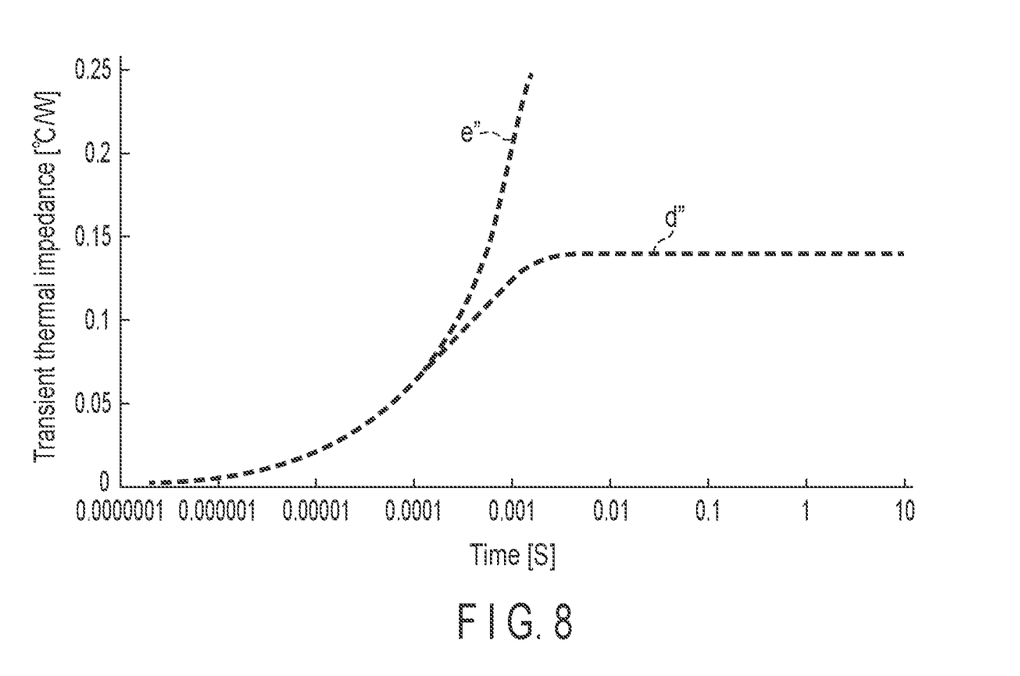
FIG. 8 is a diagram showing time-dependent changes in thermal characteristics of the semiconductor device in a heat dissipation state and an adiabatic state which are estimated by using a simulation apparatus of a comparative example.

FIG. 8 is a diagram showing time-dependent changes in thermal characteristics (simulation results) of the semiconductor device 2 in the heat dissipation state and in the adiabatic state which are estimated by using a simulation apparatus of a comparative example.

The simulation apparatus of the comparative example is different from the simulation apparatus of the present embodiment in that the simulation apparatus of the comparative example uses thermal circuit data of a thermal equivalent circuit created by omitting the fourth resistor R4, the fourth capacitor C4, the eighth resistor R8, and the eighth capacitor C8 (the thermal resistances and the thermal capacities at the final stages) from the thermal equivalent circuit 3 shown in FIG. 3.

In FIG. 8, a curve d" represents a time-dependent change in the thermal characteristics of the semiconductor device 2 in the heat dissipation state. A curve e" represents a time-dependent change in the thermal characteristics of the semiconductor device 2 in the adiabatic state.

FIG. 7 and FIG. 8 demonstrate the following facts. In the case of the heat dissipation state, the curve d" representing the simulation result substantially matches the curve d' representing the analysis result. In the case of the adiabatic state, however, the curve e" representing a simulation result does not match the curve e' representing an analysis result.

In the embodiment, the simulation result and the analysis result substantially match in the case of the adiabatic state because of the following reason.

In the embodiment, the reason is because the impedance between the terminal Tc1 and the terminal Ta in the transient state period is increased by the addition of the fourth resistor R4, the fourth capacitor C4, the eighth resistor R8, and the eighth capacitor C8. The fourth resistor R4 and the fourth capacitor C4 do not affect the impedance between the terminal Tc1 and the terminal Ta in a steady state period. In addition, the eighth resistor R8 and the eighth capacitor C8 do not affect the impedance between the terminal Tc2 and the terminal Ta in the steady state period.

In some cases, the resistance value of one of the fourth resistor R4 and the eighth resistor R8 may be substantially zero. In such a case, the one of the fourth resistor R4 and the eighth resistor R8 may be omitted. It should be noted, however, that omitting the fourth resistor R4 renders the first thermal equivalent circuit 61 a non-Cauer type. Omitting the eighth resistor R8, on the other hand, renders the second thermal equivalent circuit 62 a non-Cauer type.

Figure 9:
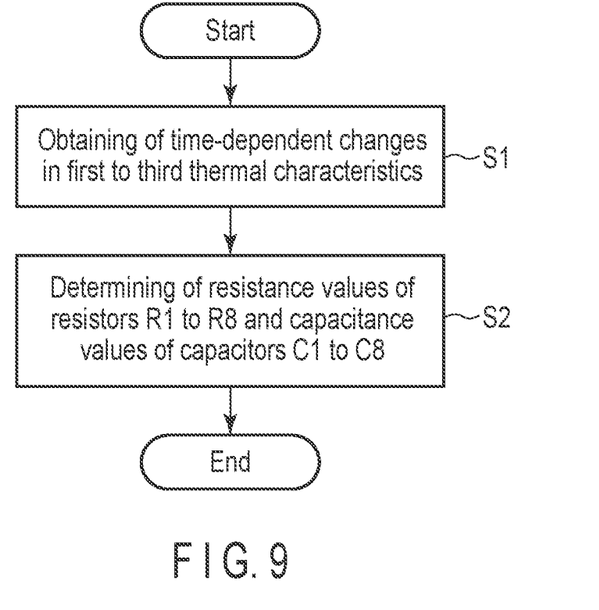
FIG. 9 is a flowchart showing a procedure of a first creation method of a thermal equivalent circuit according to an embodiment.

FIG. 9 is a flowchart showing a procedure of a first creation method of the thermal equivalent circuit 3.

First, a time-dependent change in the thermal characteristics of the semiconductor device 2 with the lower surface heat dissipation (hereinafter "a time-dependent change in first thermal characteristics"), a time-dependent change in the thermal characteristics of the semiconductor device 2 with the upper surface heat dissipation (hereinafter "a time-dependent change in second thermal characteristics"), and a time-dependent change in the thermal characteristics of the semiconductor device 2 with the double-surface heat dissipation (hereinafter "a time-dependent change in third thermal characteristics") are obtained (step S1).

Time-dependent changes in the first to third thermal characteristics are obtained by simulations or actual measurements. One or two of the first to third time-dependent changes in the thermal characteristics may be obtained by actual measurement while the rest of the first to third time-dependent changes in the thermal characteristics may be obtained by simulation. Note that, when the time-dependent change in the thermal characteristics is obtained by the actual measurement, it is preferable that influence of measurement environment of the actual measurement be removed from the measurement results.

Subsequently, the first thermal equivalent circuit 61 and the second thermal equivalent circuit 62 connected thereto are created (step S2). Note that, when reproducing a time-dependent change in the thermal characteristics in the adiabatic state is unnecessary, the resistors R4 and R8 and the capacitors C4 and C8 are not needed.

The process flow then proceeds to a step (step S3) to determine the resistance values of the resistors R1 to R4 and the capacitance values of the capacitors C1 to C4 of the first thermal equivalent circuit 61, and the resistance values of the resistors R5 to R8 and the capacitance values of the capacitors C5 to C8 of the second thermal equivalent circuit 62. Note that, when reproducing a time-dependent change in the thermal characteristics in the adiabatic state is unnecessary, the resistance values of the resistors R1 to R3, the capacitance values of the capacitors C1 to C3, the resistance values of the resistors R5 to R7, and the capacitance values of the capacitors C5 to C8 are determined.

Step S2 is executed in the following manner. The resistance values of the resistors R1 to R8 and the capacitance values of the capacitors C1 to C8 are determined, such that (i) a first difference between the time-dependent change in the thermal characteristics of the lower-surface-side part of the semiconductor device 2 that is calculated by using the first thermal equivalent circuit 61 and the second thermal equivalent circuit 62 and the time-dependent change in the first thermal characteristics falls in a predetermined first range, (ii) a second difference between the time-dependent change in the thermal characteristics of the upper-surface-side part of the semiconductor device 2 that is calculated by using the first thermal equivalent circuit 61 and the second thermal equivalent circuit 62 and the time-dependent change in the second thermal characteristics falls in a predetermined second range, and (iii) a third difference between the time-dependent change in the thermal characteristics of the lower-surface-side and upper-surface-side parts of the semiconductor device 2 that is calculated by using the first thermal equivalent circuit 61 and the second thermal equivalent circuit 62 and the time-dependent change in the third thermal characteristics falls in a predetermined third range.

The first range, the second range, and the third range are determined according to thermal characteristics (specifications) required for the semiconductor device 2. It is preferable that the resistance values of the resistors R1 to R8 and the capacitance values of the capacitors C1 to C8 be determined such that the value of the first difference approaches the lower limit value of the first range, the value of the second difference approaches the lower limit value of the second range, and the value of the third difference approaches the lower limit value of the second range.

Figure 10:
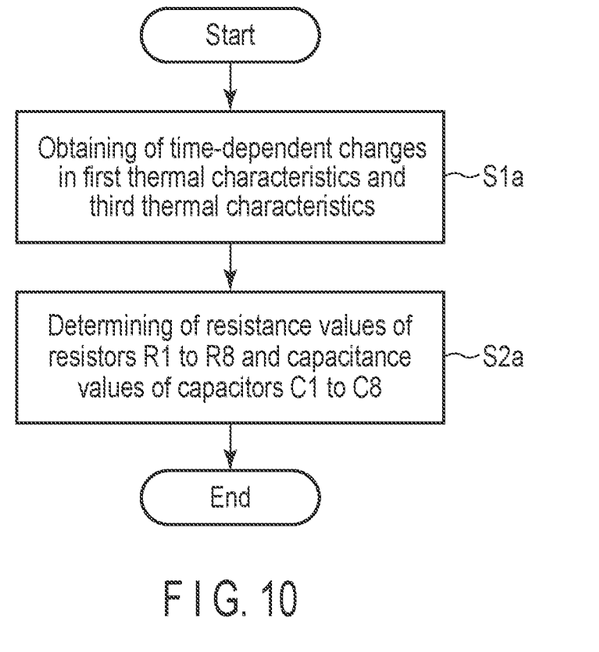
FIG. 10 is a flowchart showing a procedure of a second creation method of a thermal equivalent circuit according to an embodiment.

FIG. 10 is a flowchart showing a procedure of a second creation method of the thermal equivalent circuit 3. According to the second creation method, the time-dependent change in the second thermal characteristics (upper surface heat dissipation characteristics) is not used. The second creation method is used, for example, when creating a thermal equivalent circuit capable of reproducing the upper surface heat dissipation characteristics is unnecessary.

First, the time-dependent change in the first thermal characteristics and the time-dependent change in the third thermal characteristics are obtained (step S1a).

Subsequently, a thermal equivalent circuit including the first thermal equivalent circuit 61 and the second thermal equivalent circuit 62 connected thereto is created (step S2a).

Subsequently, the resistance values of the resistors R1 to R8 and the capacitances of the capacitors C1 to C8 are determined, such that the first difference between the time-dependent change in the thermal characteristics of the lower-surface-side part of the semiconductor device 2 that is calculated by using the first thermal equivalent circuit 61 and the second thermal equivalent circuit 62 and the time-dependent change in the first thermal characteristics falls in the predetermined first range, and the third difference between the time-dependent change in the thermal characteristics of the lower-surface-side and upper-surface-side parts of the semiconductor device 2 that is calculated by using the first thermal equivalent circuit 61 and the second thermal equivalent circuit 62 and the time-dependent change in the third thermal characteristics falls in the predetermined third range.

Figure 11:
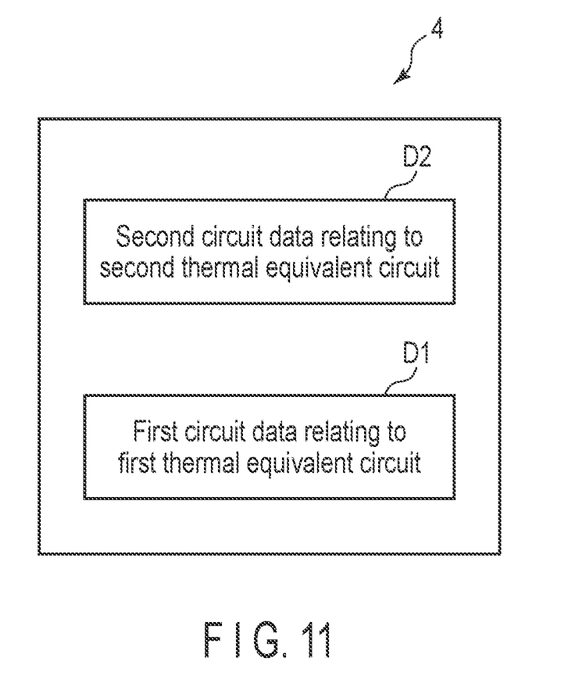
FIG. 11 is a diagram showing a data structure of a thermal equivalent circuit that is used for a simulation apparatus according to an embodiment.

FIG. 11 is a diagram showing a data structure 4 of the thermal equivalent circuit 3 used for a simulation apparatus 1.

As described above, the thermal equivalent circuit 3 includes the first thermal equivalent circuit 61 corresponding to the upper-surface-side part of the semiconductor device 2, and the second thermal equivalent circuit 62 connected to the first thermal equivalent circuit 61 and corresponding to the lower-surface-side part of the semiconductor device 2. The data structure 4 includes first circuit data D1 relating to the first thermal equivalent circuit 61 and second circuit data D2 relating to the second thermal equivalent circuit 62.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A creation method of a thermal equivalent circuit, the method comprising:
   obtaining a first time-dependent change in thermal characteristics of a lower-surface-side part of a semiconductor device, a second time-dependent change in thermal characteristics of an upper-surface-side part of the semiconductor device, and a third time-dependent change in thermal characteristics of the lower-surface-side and upper-surface-side parts of the semiconductor device;
   creating a first thermal equivalent circuit and a second thermal equivalent circuit connected to the first thermal equivalent circuit, the first thermal equivalent circuit including a plurality of first resistors and a plurality of first capacitors and corresponding to the lower-surface-side part of the semiconductor device, and second thermal equivalent circuit including a plurality of second resistors and a plurality of second capacitors and corresponding to the upper-surface-side part of the semiconductor device; and
   determining resistance values of the plurality of first resistors, capacitance values of the plurality of first capacitors, resistance values of the plurality of second resistors and capacitance values of the plurality of second capacitors, such that a difference between a time-dependent change in thermal characteristics of the lower-surface-side part of the semiconductor device that is calculated by using the first and second thermal equivalent circuits and the obtained first time-dependent change in the thermal characteristics falls in a predetermined first range, a difference between a time-dependent change in thermal characteristics of the upper-surface-side part of the semiconductor device that is calculated by using the first and second thermal equivalent circuits and the obtained first thermal equivalent circuit falls in a predetermined second range, and a difference between a time-dependent change in thermal characteristics of the lower-surface-side and upper-surface-side parts of the semiconductor device that is calculated by using the first and second thermal equivalent circuits and the obtained third time-dependent change in the thermal characteristics falls in a predetermined third range.

2. The creation method of claim 1, wherein obtaining the third time-dependent change in the thermal characteristics is omitted.

* * * * *